(12) United States Patent
Park

(10) Patent No.: US 11,110,027 B2
(45) Date of Patent: Sep. 7, 2021

(54) VISION TRAINING DEVICE FOR IMPROVING FUSIONAL VERGENCE

(71) Applicant: EDENLUX CORPORATION, Changwon-si (KR)

(72) Inventor: Sungyong Park, Busan (KR)

(73) Assignee: EDENLUX CORPORATION, Changwon-si (KR)

( * ) Notice: Subject to any disclaimer, the term of this patent is extended or adjusted under 35 U.S.C. 154(b) by 244 days.

(21) Appl. No.: 16/439,599

(22) Filed: Jun. 12, 2019

(65) Prior Publication Data

US 2019/0290529 A1 Sep. 26, 2019

Related U.S. Application Data

(63) Continuation of application No. PCT/KR2016/014735, filed on Dec. 15, 2016.

(51) Int. Cl.
*A61H 5/00* (2006.01)
*A61F 9/02* (2006.01)
*A61B 3/032* (2006.01)
*A61B 3/04* (2006.01)

(52) U.S. Cl.
CPC ............. *A61H 5/00* (2013.01); *A61B 3/032* (2013.01); *A61B 3/04* (2013.01); *A61F 9/022* (2013.01); *A61F 9/027* (2013.01); *A61F 9/029* (2013.01); *A61H 2201/5043* (2013.01)

(58) Field of Classification Search
CPC .... A61B 3/00; A61B 3/04; A61B 3/03; A61B 3/002; A61H 5/00; A61F 9/022; A61F 9/027; A61F 9/029; A61F 2201/5043

USPC ............... 351/203, 246, 200; 601/37
See application file for complete search history.

(56) References Cited

U.S. PATENT DOCUMENTS

| 4,756,305 A | 7/1988 | Mateik et al. |
| 5,478,239 A | 12/1995 | Fuerst et al. |
| 8,668,334 B2 * | 3/2014 | Krenik ................ A61B 3/0033 351/205 |
| 2004/0075811 A1 | 4/2004 | Liberman |

(Continued)

FOREIGN PATENT DOCUMENTS

| JP | H08257077 A | 10/1996 |
| JP | 2009000368 A | 1/2009 |
| JP | 2010511486 | 4/2010 |

(Continued)

OTHER PUBLICATIONS

Japanese Patent Office, Notice of Reasons for Rejection dated Dec. 17, 2020 in Japanese patent application No. 2019-532010, 8 pages total.

(Continued)

*Primary Examiner* — Hung X Dang
(74) *Attorney, Agent, or Firm* — Trop, Pruner & Hu, P.C.

(57) ABSTRACT

At least one of the first display and a second display move at least one of the left eye image and the right eye image such that a distance between the left eye image and the right eye image is increased. A separation confirmation signal is received indicating that the image focuses of the image do not coincide with each other in terms of fusion. Fusional amplitude information is stored indicating a separation distance between the left eye image and the right eye image when the image separation confirmation is input.

18 Claims, 8 Drawing Sheets

(56) References Cited

U.S. PATENT DOCUMENTS

2013/0169929 A1    7/2013  Fateh

FOREIGN PATENT DOCUMENTS

| JP | 201295694 A | 5/2021 |
|----|-------------|--------|
| KR | 20120139455 | 12/2012 |
| WO | WO2007037432 | 4/2007 |
| WO | WO2009053917 | 4/2009 |
| WO | WO2015068168 | 5/2015 |
| WO | WO2016078911 | 5/2016 |

OTHER PUBLICATIONS

European Patent Office, Supplementary European Search Report dated Jul. 16, 2020 in European patent application No. 16923710.4, 12 pages total.
Chinese Patent Office, First Office Action dated Mar. 1, 2021 in Chinese Patent Application No. 201680091667.4 (4 pages).
Japanese Patent Office, Notices of Reasons for Rejection dated Jul. 13, 2021 in Japanese Patent Application No. 2019532010 (9 pages).

\* cited by examiner

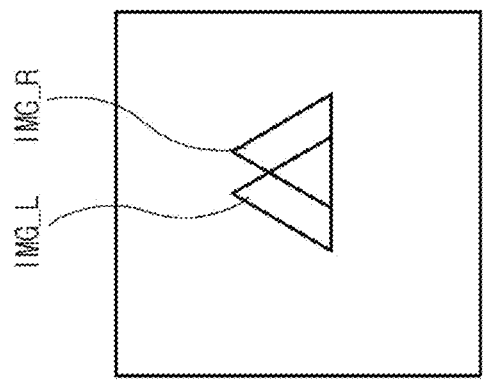
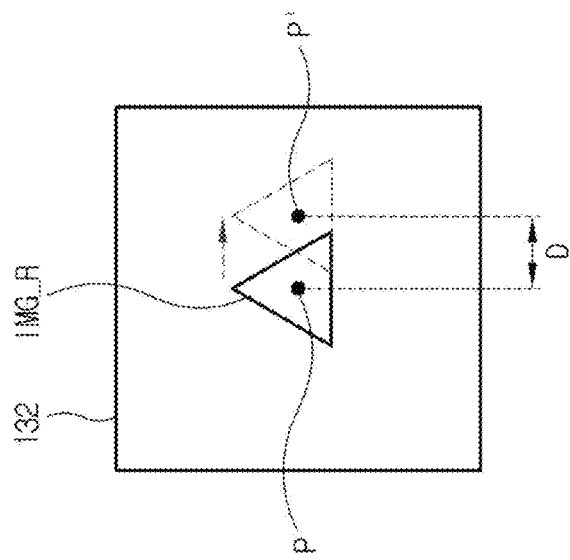
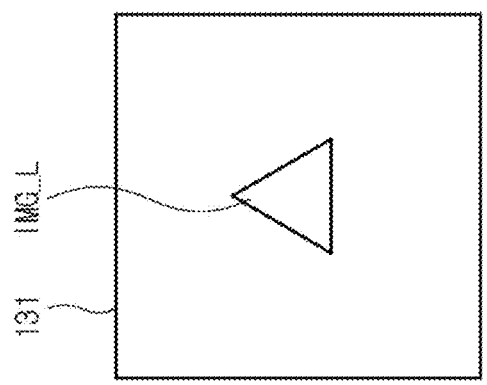
FIG. 6B
FIG. 6A

VISION TRAINING DEVICE FOR IMPROVING FUSIONAL VERGENCE

CROSS REFERENCE TO RELATED APPLICATION

This application is a continuation application of PCT/KR2016/014735, which was filed on Dec. 15, 2016, the entire contents of which are incorporated herein in their entirety.

BACKGROUND

This disclosure relates to a vision training device for improving a fusional vergence.

Out of human visual functions, fusional vergence is a function in which images which are separately recognized by the left eye and the right eye are fused to produce binocular vision. If such fusional vergence is weaker than normal fusional vergence, the eyes easily feel tired. In severe cases, diplopia, which is a simultaneous perception of two images, of a single object may occur.

U.S. Patent Publication No. 20120069296 discloses a system for treating a binocular vision disorder. The system includes two separate displays corresponding to the left and right eyes and changes a viewing angle of an image displayed by each display to improve the fusional vergence.

However, training is performed by a general method without the fusional vergence specific to the user, and thus the effect of the training is not great. Also, the vision training device according to the related art has a problem in that the fusional vergence specific to the user, which is a parameter that can represent the status of personal vision, is not measured and managed.

BRIEF SUMMARY

In an embodiment, a vision training device includes a left display, a right display, a user input unit, and a controller. The left display is configured to provide a left eye image corresponding to a left eye of a user. The right display is configured to provide and a right eye image corresponding to a right eye of the user. The controller is configured to control at least one of the left display and the right display to move at least one of the left eye image and the right eye image such that the left eye image and the right eye image are spaced apart from each other and the image focuses of the images coincide with each other in terms of fusion, control at least one of the left display and the right display to move at least one of the left eye image and the right eye image such that a distance between the left eye image and the right eye image is increased, receive, from the user input unit, a separation confirmation signal indicating that the image focuses of the image do not coincide with each other in terms of fusion, and store, as fusional amplitude information, information indicating a separation distance between the left eye image and the right eye image when the image separation confirmation is input through the user input unit.

In an embodiment, a vision training method includes: displaying, on a left display, a left eye image corresponding to a left eye of a user; displaying, on a right display, a right eye image corresponding to a right eye of the user; controlling at least one of the left display and the right display to move at least one of the left eye image and the right eye image such that the left eye image and the right eye image are spaced apart from each other and the image focuses of the images coincide with each other in terms of fusion; controlling at least one of the left display and the right display to move at least one of the left eye image and the right eye image such that a distance between the left eye image and the right eye image is increased; receiving, from a user input unit, a separation confirmation signal indicating that the image focuses of the image do not coincide with each other in terms of fusion; and storing, as fusional amplitude information, information indicating a separation distance between the left eye image and the right eye image when the image separation confirmation is input through the user input unit.

BRIEF DESCRIPTION OF THE DRAWINGS

FIG. 6A is a reference view for explaining a measurement mode in FIG. 5.

FIG. 6B is a reference view for explaining a measurement mode in FIG. 5.

DETAILED DESCRIPTION

Figure 1:
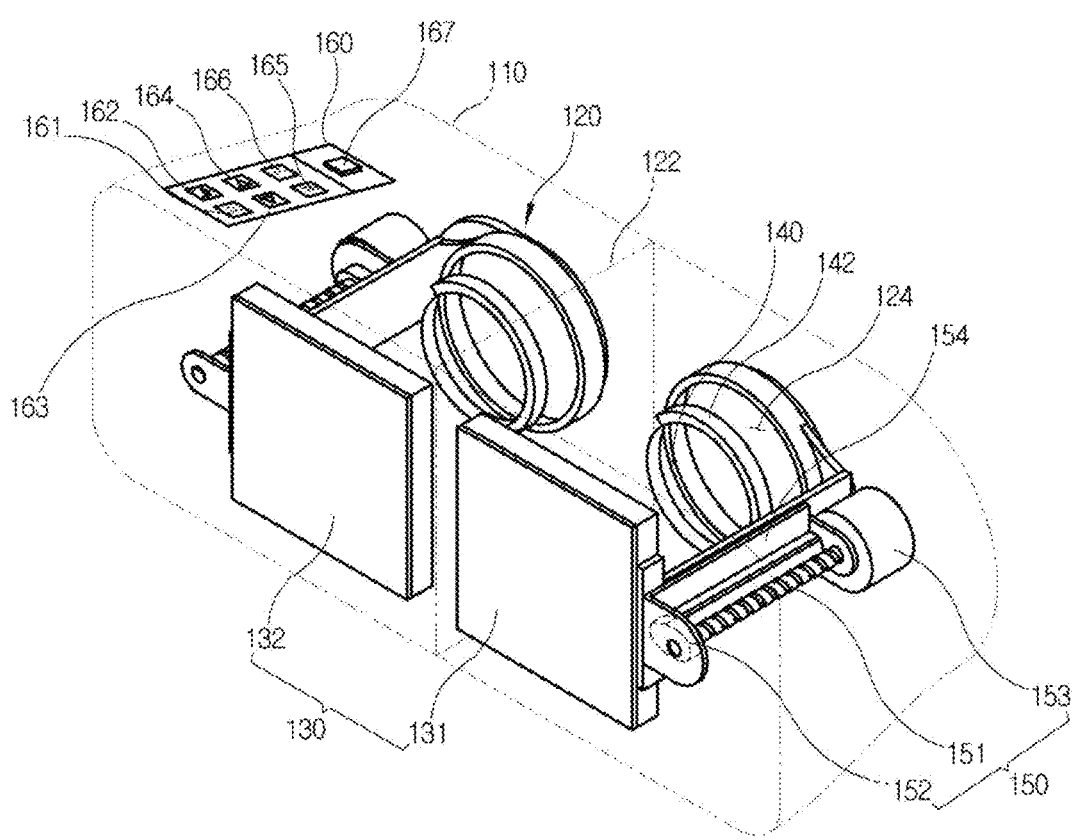
FIG. 1 is a perspective view of a vision training device according to an embodiment of the present disclosure.

According to an aspect, a vision training device is capable of measuring and managing the fusional vergence of the user.

According to another aspect, a vision training device is capable of providing vision training in which the measured fusional vergence of the user is reflected.

The above-described exemplary and non-limiting aspects may be provided by a vision training device including a display unit that provides a left eye image corresponding to a left eye of a user and a right eye image corresponding to a right eye of the user, a user input unit, and a controller that controls the display unit such that at least one of the left eye image and the right eye image is apart from the other after the left and right eye images are provided in a state in which Purkinje image focuses of the images coincide with each other in terms of fusion, and stores, as fusional amplitude information, information indicating a separation distance between the left eye image and the right eye image when an image separation confirmation is input through the user input unit.

According to an embodiment of the present disclosure as above, the display unit may include a left display that provides the left eye image and a right display that provides the right eye image. In this case, a filter for separating a visual field is not required, and thus a vision training device with a simpler configuration may be implemented.

The controller controls the left and right display units such that at least one of the left eye image and the right eye image is moved to get closer to the other after the left and right eye images are provided in a state in which the Purkinje image focuses of the images do not coincide with each other in terms of fusion, and determines that the Purkinje image focuses of the images coincide with each other in terms of fusion when a focus consistency confirmation signal is input through the user input unit during the movement. Accordingly, the measurement mode may be performed more accurately.

The left eye image and the right eye image are provided to a single display device, and the vision training device further comprises a mutually relative fusion/separation filter that provides the left eye image and the right eye image to the left eye and the right eye, respectively. Accordingly, the vision training can be performed with a simpler configuration.

The controller sets a training range in which fusional vergence training is performed by using the fusional amplitude information of the user and moves at least one of the left eye image and the right eye image to be apart from and get closer to the other within the set training range. Accordingly, vision training in which the status of the personal vision of the user is considered can be performed.

The training range may be set to include the separation distance corresponding to the fusional amplitude information, and in this case, the effect of the vision training can be increased.

As described above, according to the present disclosure, it is possible to measure and manage the fusional vergence of the user. Also, the customized vision training for improving the fusional vergence in which the measured fusional vergence is considered is provided, so that the fusional vergence of the user can be improved more effectively.

Hereinafter, exemplary embodiments of the present disclosure will be described in detail with reference to the appended drawings.

FIG. 1 is a perspective view of a vision training device according to an embodiment of the present disclosure. The vision training device includes a pair of vision training units 120 that are arranged on left and right sides in a housing 110 indicated by an imaginary line. A partition panel 122 is disposed between the pair of vision training units 120 to partition visual fields of the left eye and the right eye so that the visual fields of the eyes do not overlap with each other.

The vision training units 120 include an eyepiece opening 124 and a display unit 130 that are arranged to face each other in a line of sight direction. The display unit 130 includes a left display 131 corresponding to the left eye and a right display 132 corresponding to the right eye. Each of the left and right displays 131 and 132 displays an image thereon for vision training, and the user visually recognizes the images displayed by the left and right displays 131 and 132 through the eyepiece openings 124.

A user input unit 160 may be located on an upper surface of the housing 110. The user input unit 160 receives a user input from the user. The user selects a mode such as a measurement mode and a training mode and inputs a user confirmation through the user input unit 160. In the housing 110, a strap or temples of glasses may be installed so that the user can wear the vision training device on his/her head.

The left display 131 of the display unit 130 displays a left eye image in the line of sight direction of the left eye of the user. The right display 132 displays a right eye image in the line of sight direction of the right eye of the user. Examples of the left eye image and the right eye image displayed in this manner include a still image such as a dot, a line, a landscape image, a figure, or a geometric pattern, a video, and a 3D image. Also, the image may be a color image. To provide such image, the display unit 130 may include an electronic display device such as a liquid crystal display (LCD) or an organic light emitting diode (OLED). The display unit 130 may be implemented such that an external display device such as a smartphone may be mounted in the vision training device.

A lens 140 is held by a lens holder 142 and is arranged between the eyepiece opening 124 and the display unit 130. The user recognizes an image displayed in the line of sight direction through the eyepiece opening 124 and the lens 140. The lens 140 may be a convex lens. The convex lens extends the perspective of an image by changing a focal length between the eye of the user and an image so that the user can recognize as if the image is at a distance farther than an actual distance. Such a lens may be replaced by a mirror that refracts an optical path between the eyes and an image. In this case, the mirrors extend the perspective of an image by extending a distance of a visual field between the eye and the image to be larger than an actual distance. The lens 140 may be or include a polarizing lens or a color lens to separate an image which is recognized by both eyes into a left eye image and a right eye image if necessary.

A display mover 150 moves the left and right displays 131 and 132 of the display unit 130 in forward and backward directions along the line of sight direction of the user. The display mover 150 includes a lead screw 151, a moving body 152 movably coupled to the lead screw 151, and a driving motor 153 rotatably driving the lead screw 151.

The lead screw 151 is rotatably installed in a fixing support 154 installed in the housing 110 and is rotatably driven by the driving motor 153. A rotational movement of the lead screw 151 is converted into a sliding movement of the moving body 152 in the forward or backward direction. The moving body 152 is coupled with the display unit 130 so that the display unit 130 reciprocates in the forward or backward direction with the rotational movement of the lead screw 151.

The partition panel 122 is disposed in the housing 110 and separates the inside of the housing 110 into two parts corresponding to the left eye and the right eye. The partition panel 122 causes the left eye of the user to recognize only the left eye image displayed by the left display 131 and causes the right eye of the user to recognize only the right eye image displayed by the right display 132.

The vision training device according to the embodiment of the present disclosure described above includes the two individual display devices, and the two display devices function as the left display 131 for providing the left eye image to the left eye of the user and the right display 132 for providing the right eye image to the right eye of the user. In an embodiment, the vision training device employs two independent display devices, but a similar function can be implemented with a single display device. In this case, the single display device has a screen divided into left and right sides and displays the left eye image and the right eye image so that they are apart from each other. A region of the single display device on which the left eye image is displayed corresponds to the left display, and the other region of the single display device on which the right eye image is displayed corresponds to the right display.

Figure 2:
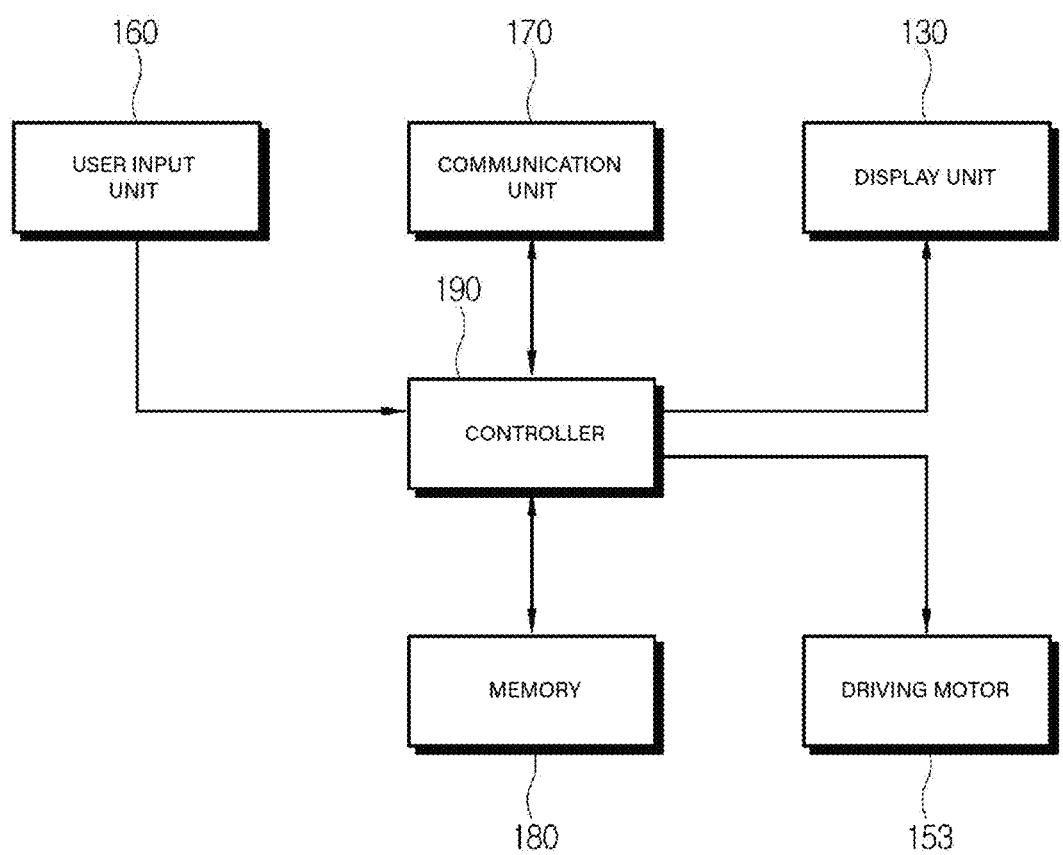
FIG. 2 is a control block diagram of a vision training device according to an embodiment of the present disclosure.

FIG. 2 is a control block diagram of the vision training device according to the present disclosure.

The user input unit 160 is disposed on an upper surface or a side surface of the vision training device, and a controller 190 receives information or a condition input by the user through the user input unit 160. The user input unit 160 includes a plurality of user input buttons 161, 162, 163, 164, 165, 166, and 167. Examples of the buttons include a power input button 161, a user selection button 162, a forward movement button 163, a backward movement button 164, a measurement mode selection button 165, a training mode selection button 166, and a focus coincidence mode button 167. The user input which is input through the user input unit 160 is received by the controller 190, and then the controller 190 performs control such that the vision training device performs an operation corresponding to the user input. The user input unit 160 having the button-like form may be replaced with a keypad, a touch screen, or the like. In an embodiment, the user input unit 160 is attached to the vision training device, but the user input unit 160 may be implemented by a wired or wireless remote controller or may be replaced with an application of a mobile device such as a smartphone. The user input unit 160 may be implemented by a voice recognition technique using a microphone.

A communication unit 170 communicates with an external device such as a smartphone, a tablet PC, or a user server in a wired or wireless manner. The vision training device may transmit data to an external device or receive data from an external device through the communication unit 170.

A memory 180 stores user information, fusional amplitude information, training data, and various types of data necessary for the operation of the vision training device.

The controller 190 controls the operation of the vision training device according to the embodiment of the present disclosure in general. The controller 190 controls the movement of the display unit 130 by controlling the driving motor 153. The controller 190 may control the left display 131 and the right display 132 such that they display the left eye image and the right eye image thereon or a displayed image is moved within the display.

The vision training device may be driven using a battery installed therein as a power source or may be driven by an external power source connected thereto.

The vision training device according to an embodiment of the present disclosure can be used not only when the eyes of the user are in the corrected state but also when the eyes of the user are not in the corrected state. When the eyes of the user are not in the corrected state, the user can move the left display 131 and the right display 132 and change the focal length by pressing the forward movement button 163 or the backward movement button 164 of the user input unit 160, so that the eyes of the user enter the corrected state, and the user can perform the vision training without wearing glasses.

Figure 3:
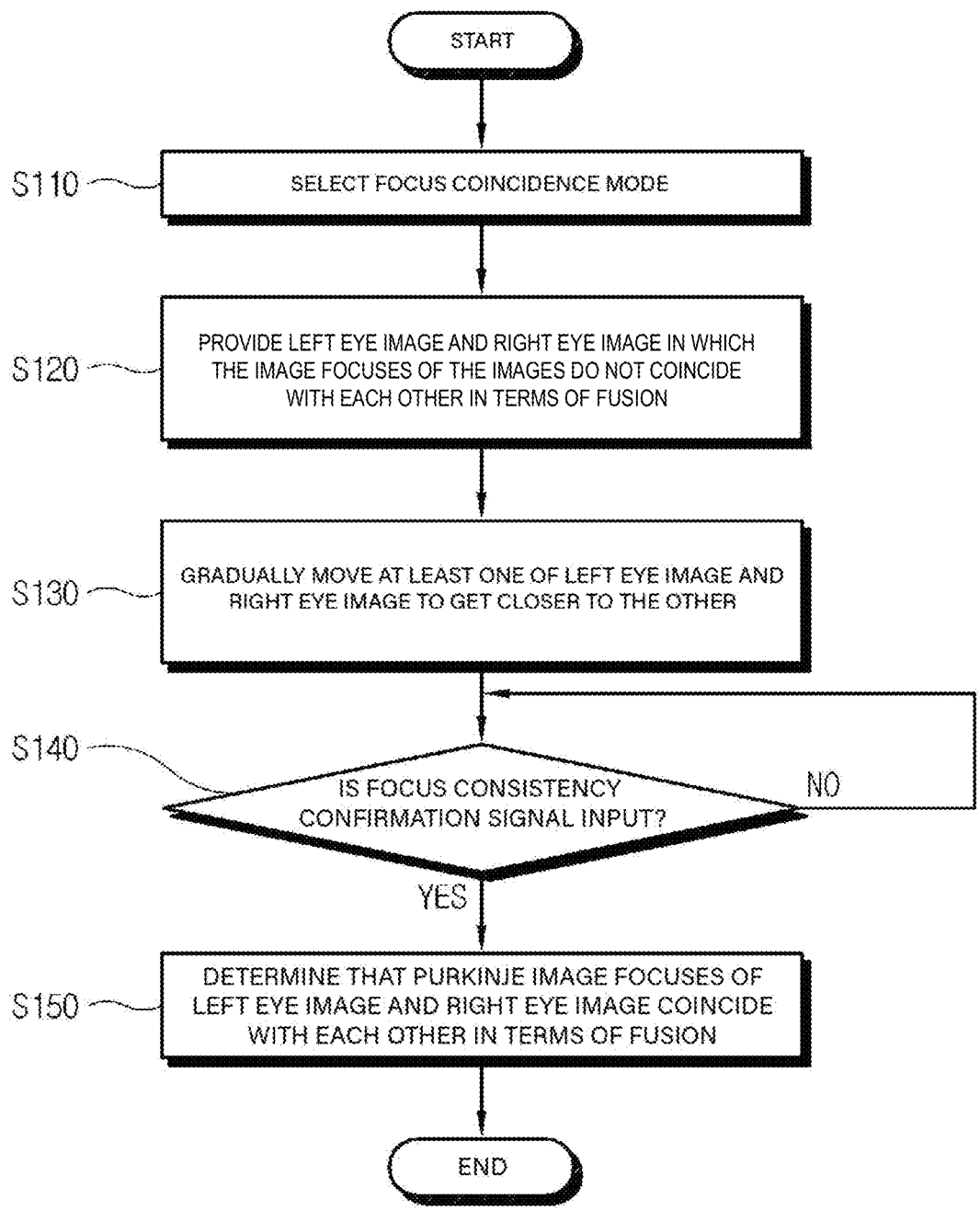
FIG. 3 is a flowchart showing an example of a focus coincidence mode process of a vision training device according to the present disclosure.

FIG. 3 is a flowchart showing an example of a focus coincidence mode operation of the vision training device according to an embodiment of the present disclosure. FIG. 4 are reference views for explaining the focus coincidence mode in FIG. 3.

The vision training device according to an embodiment of the present disclosure includes the two individual displays. In this case, it is desirable to perform an image focus coincidence mode operation of causing a left eye target image to be provided to the left display 131 and a right eye target image to be provided the right display 132 to coincide with each other in terms of fusion to provide a measurement of the user before training is performed.

When the left and right image focuses coincide with each other in terms of fusion, it means a state in which, although the left eye of the user recognizes only the left eye image, and the right eye recognizes only the right eye image, the user actually recognizes them as a single image in which the left and right eye images overlap by the fusional vergence which is one of visual functions.

When the user presses the power input button 161 of the user input unit 160, electric power is supplied to the vision training device. The user wears the vision training device and then selects the focus coincidence mode by pressing the focus coincidence mode button 167 of the user input unit 160 (S110).

When the focus coincidence mode is selected, the controller 190 controls the left display 131 and the right display 132 so that a left eye image IMG_L and a right eye image IMG_R are provided in a sufficiently separated state in which the image focuses of the images do not coincide with each other in terms of fusion (S120). In the state in which the image focuses do not coincide with each other in terms of fusion, the eyes of the user recognize two separate images as shown by the left eye image IMG_L and the right eye image IMG_R in FIG. 4A.

Figure 4A:
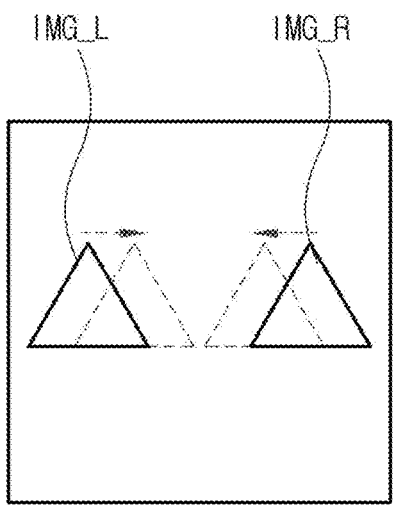
FIG. 4A is a reference view for explaining the focus coincidence mode in FIG. 3.

Thereafter, the controller 190 controls at least one of the left display 131 or the right display 132 such that the left eye image IMG_L and the right image IMG_R gradually get closer to each other as illustrated by the arrows in FIG. 4A (S130). In an example, the left image is translated to the right on the left display 131. In an example, the right image is translated to the left on the right display 132. In an example both the left and right images are respectively translated inwardly on the displays.

Figure 4B:
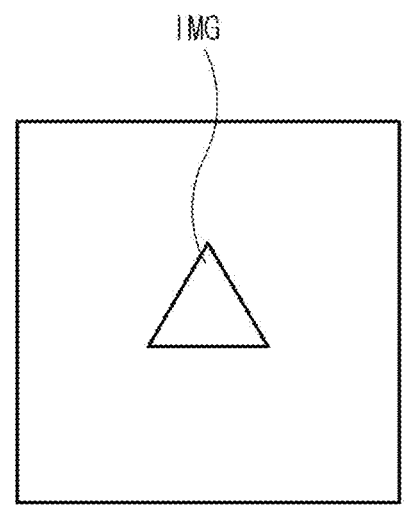
FIG. 4B is a reference view for explaining the focus coincidence mode in FIG. 3.

The controller 190 confirms whether or not a focus consistency confirmation signal is input through the user input unit 160 (S140). The focus consistency confirmation signal refers to a signal that is input by the user pressing the user confirmation button 162 of the user input unit 160 when the eyes of the user recognize the left eye image IMG_L and the right eye image IMG_R as a combined a single image IMG as shown in FIG. 4B.

When the focus consistency confirmation signal is input through the user input unit 160, the controller 190 determines that the image focus of the left eye image IMG_L corresponding to the left eye of the user and image focus of the right eye image IMG_R corresponding to the right eye coincide with each other in terms of fusion (S150). The controller 190 stores location information of the left eye image IMG_L provided to the left display 131 and location information of the right eye image IMG_R provided to the right display 132 at which the image focuses coincide with each other in terms of fusion for the measurement mode. For example, the controller may store a distance (e.g., in mm or pixels) between the images or with respect to a reference point.

Figure 5:
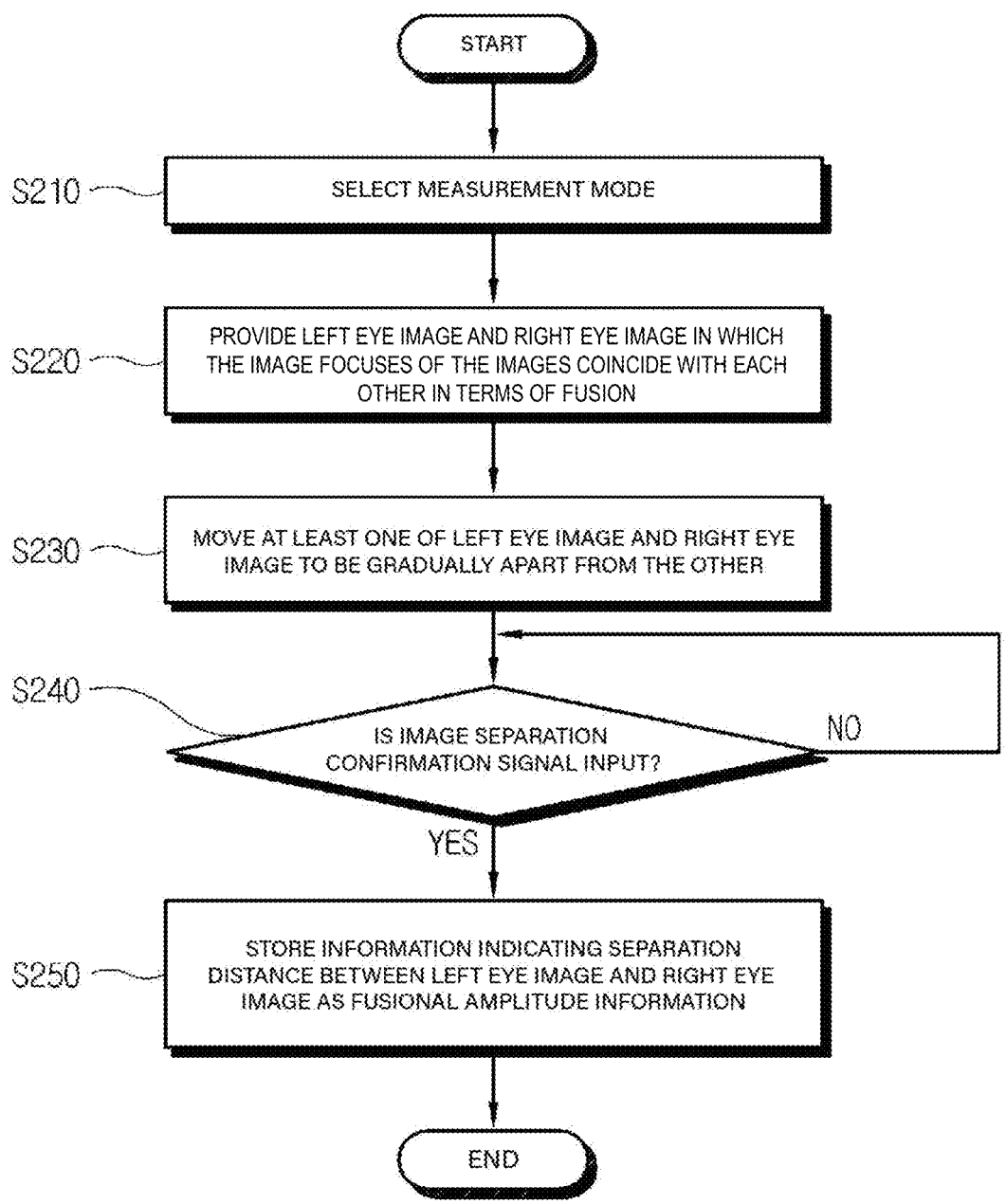
FIG. 5 is a flowchart showing an example of a measurement mode operation of a vision training device according to an embodiment of the present disclosure.

FIG. 5 is a flowchart showing an example of a measurement mode operation of the vision training device according to an embodiment of the present disclosure. FIG. 6 are reference views for explaining the measurement mode in FIG. 5. The measurement mode operation of the vision training device according to an embodiment of the present disclosure will be described below with reference to FIGS. 5 and 6.

When the user presses the power input button 161 of the user input unit 160, electric power is supplied to the vision training device. The user wears the vision training device and then selects the measurement mode by pressing the measurement mode selection button 165 of the user input unit 160 (S110).

When the measurement mode is selected, the controller 190 controls the left display 131 and the right display 132 such that the left eye image IMG_L and the right eye image IMG_R are displayed on the left and right displays 131 and 143 in the state in which the image focuses of the left eye image IMG_L and the right eye image IMG_R coincide with each other in terms of fusion using the location information stored in the focus coincidence mode (S220). When the measurement mode is performed by the user after the focus coincidence mode, the left eye image IMG_L and the right eye image IMG_R are already provided to the left and right displays 131 and 132 in the state in which the image focuses coincide with each other in terms of fusion, and thus step S220 may be omitted. When the left eye image IMG_L and right eye image IMG_R are provided to the left and right displays 131 and 132 in the state in which the image focuses coincide with each other in terms of fusion, the user recognizes the single image IMG through both eyes as illustrated in FIG. 4B.

Thereafter, the controller 190 controls the display unit 130 such that at least one of the left eye image IMG_L and the right eye image IMG_R is moved apart from the other (S230). The following description will proceed with an example in which the right eye image IMG_R is moved from the left eye image IMG_L as illustrated in FIG. 6A. When the right eye image IMG_R is gradually moved apart from the left eye image IMG_L, the user still recognizes a single image within a certain separation distance depending on the specific fusional vergence of the user.

As the right eye image IMG_R is moved farther apart from the left eye image IMG_L, the user recognizes two images as illustrated in FIG. 6B.

The controller 190 confirms whether or not an image separation confirmation signal is input through the user input unit 160 (S240). The user inputs the image separation confirmation signal through the user input unit 160 when the user recognizes the two images as illustrated in FIG. 6B. The image separation confirmation signal refers to a signal that is input by the user pressing the user confirmation button 162 when the left eye image IMG_L and the right eye image IMG_R which had been recognized as a single image are separately recognized.

When the image separation confirmation signal is input through the user input unit 160, the controller 190 stores, as the fusional amplitude information, information indicating a separation distance D, for example, of the right eye image IMG_R. For example, the controller may store a distance (e.g., in mm or pixels) between the images or with respect to a reference point.

The separation distance D refers to a distance between a fixation point P before the right eye image IMG_R is moved and a fixation point P' after the right eye image IMG_R is moved when the image separation confirmation is input after such movement. The fixation point P may be set at a position of an image to be moved out of the left eye image IMG_L or the right eye image IMG_R.

The vision training device according to an embodiment of the present disclosure can measure the fusional amplitude information specific to the user since the measurement mode is performed after the focus coincidence mode. The fusional amplitude information is an element related to the fusional vergence among the visual functions of the user and can be used as an important parameter for evaluating the status of personal vision of the user. Also, the status of personal vision of the user is detected through the measurement mode, and the customized vision training in which the detected status of personal vision of the user is considered is provided, so that the effect of improving the vision of the user is increased.

The vision training device according to an embodiment of the present disclosure as shown in FIG. 1 separately provides the left eye image and the right eye image to the left eye of the user and the right eye through the two individual display devices. The vision training device may be implemented as a wearable device that may be worn by the user on the head. In the case of the wearable device, it may be difficult to provide a sufficient distance between the eyes of the user and the display device for separation and recognition of images, and thus the images may be provided to both eyes using two display devices.

However, if a sufficient distance, for example, 30 cm or more can be provided between the eyes of the user and the display device, a single display device may be employed in the vision training device.

Figure 7:
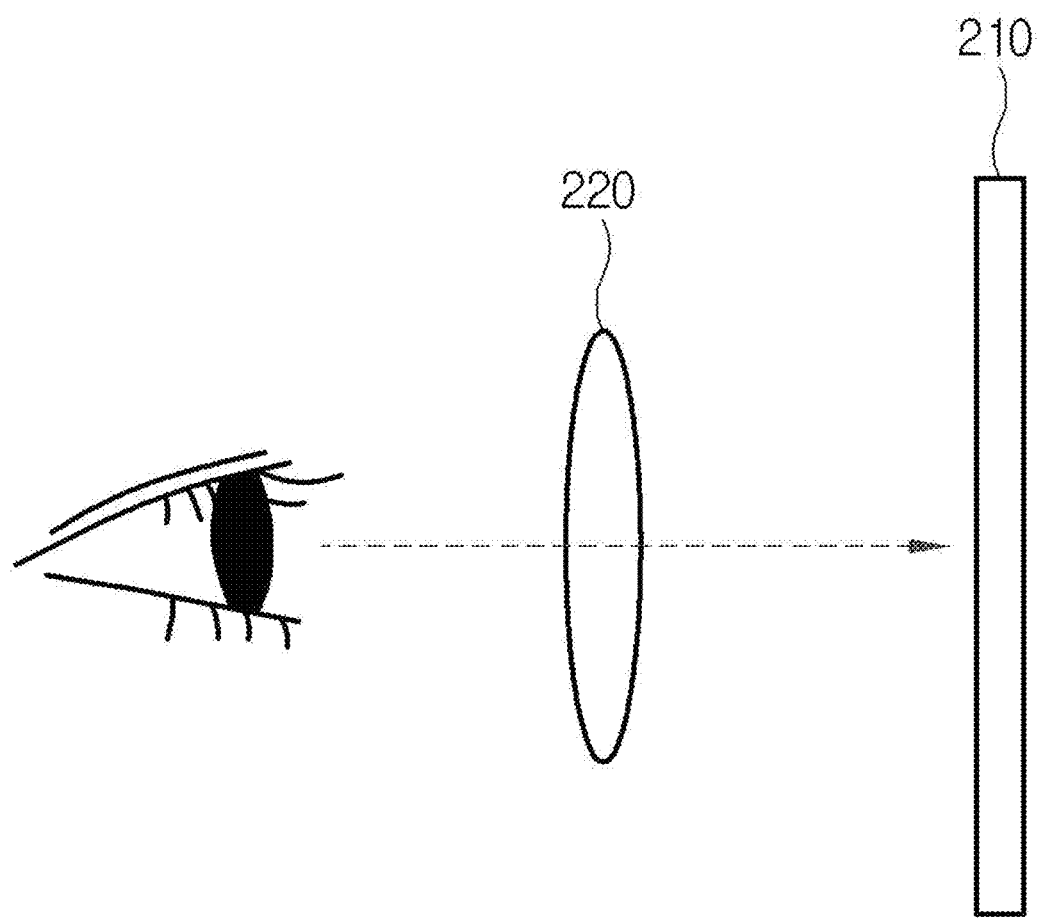
FIG. 7 is a schematic view of a vision training device according to another embodiment of the present disclosure.

FIG. 7 is a schematic view of a vision training device according to another embodiment of the present disclosure. The vision training device according to another embodiment of the present disclosure includes a single display device.

The vision training device may include a single display device 210 that is disposed at a sufficient distance, e.g. 30 cm or more from the eyes of the user and a fusion/separation filter 220 which is disposed in front of the eyes of the user. In this case, the controller 190 in FIG. 2 controls the display device 210 such that the left eye image and the right eye image are provided in an overlapping state so that the left eye image and the right eye image may be provided in the state in which the image focuses of the images coincide with each other in terms of fusion. Therefore, the vision training device need not necessarily perform the focus coincidence mode operation before the measurement mode.

The fusion/separation filter 220 may include filters capable of performing a function of enabling the left and right eyes to recognize the left eye image and the right eye image in the overlapping state, respectively. For example, when the left eye image is green and the right eye image is red, a red/green filter enables the left eye to recognize only the left eye image of green and enables the right eye to recognize only the right eye image of red. Alternatively, the fusion/separation filter 220 may include a polarizing filter which transmits only light with a certain directivity, and the left eye image and the right eye image are separately provided to the left eye and the right eye of the user, respectively. In this case, a polarizing filter corresponding to the left eye and a polarizing filter corresponding to the right eye may have different directivities.

Although the vision training device according to another embodiment of the present disclosure has been described as including the display device 210 and the fusion/separation filter 220, and the display device 210 and the fusion/separation filter 220 may be replaced with a polarizing display device. In this case, the polarizing display may perform both display and separation of images.

The measurement mode of the vision training device is similar to that of the vision training device in FIG. 1, and thus detailed description of the measurement mode is here omitted.

The vision training device may be implemented by a simple configuration such as a display or buttons of a smartphone, the red/green filter, or the like, and thus the vision training device can measure the fusional amplitude information of the user regardless of a time or a place.

Figure 8:
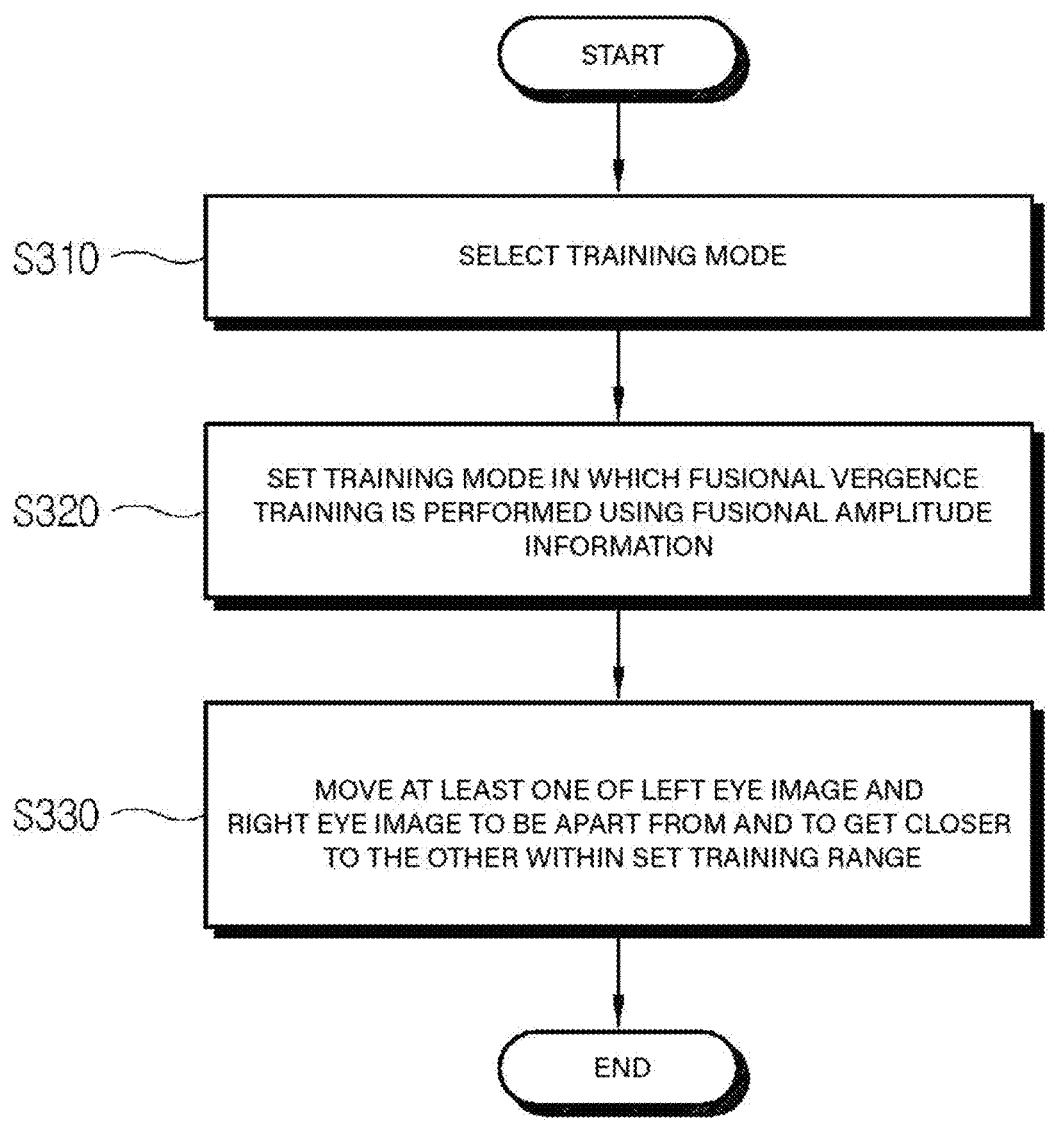
FIG. 8 is a flowchart showing an example of a training mode operation of a vision training device according to the present disclosure.

FIG. 8 is a flowchart showing an example of a training mode operation of the vision training device according to an embodiment of the present disclosure.

When the user presses the power input button 161 of the user input unit 160, electric power is supplied to the vision training device. Thereafter, the user wears the vision training device on the head and then selects the training mode by pressing the training mode selection button 166 of the user input unit 160 (S310).

When the training mode is selected, the controller 190 sets a training range in which fusional vergence training is performed by using the stored fusional amplitude information (S320). The training range refers to a movement range in which at least one of the left eye image and the right eye image is apart from the other and is moved to be closer to the other. It is desirable for the training range to include a separation distance corresponding to the fusional amplitude information measured in the measurement mode. For example, when the training range is set to have a width from on the fixation point P' after the movement in FIG. 6A, the effect of improving the fusional vergence through the training can be increased.

Thereafter, the controller 190 controls the display such that one of the left eye image and the right eye image is moved to be closer to the other.

With the training mode, the image recognized by both eyes of the user is recognized alternately in the fusion state and the non-fusion state, so that the fusional vergence of the user is improved.

While various embodiments in accordance with the disclosed principles have been described above, it should be understood that they have been presented by way of example only, and are not limiting.

Furthermore, the above advantages and features are provided in described embodiments, but shall not limit the application of such issued claims to processes and structures accomplishing any or all of the above advantages.

Although the invention(s) is/are described herein with reference to specific embodiments, various modifications and changes can be made without departing from the scope of the disclosure. Accordingly, the specification and figures are to be regarded in an illustrative rather than a restrictive sense, and all such modifications are intended to be included within the scope of the present disclosure. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms "a" and "an" are defined as one or more unless stated otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

The invention claimed is:

1. A vision training device, comprising:
a first display configured to provide a left eye image corresponding to a left eye of a user;
a second display configured to provide a right eye image corresponding to a right eye of the user; and
a controller configured to
control at least one of the first display and the second display to move at least one of the left eye image and the right eye image such that image focuses of the left and right eye images coincide with each other in terms of fusion,
control at least one of the first display and the second display to move at least one of the left eye image and the right eye image such that a distance between the left eye image and the right eye image is increased,
receive a separation confirmation signal indicating that the image focuses do not coincide with each other in terms of fusion, and
store, as fusional amplitude information, information indicating a separation distance between the left eye image and the right eye image when the separation confirmation signal is received.

2. The vision training device according to claim 1, further comprising a display unit that includes the first display and the second display.

3. The vision training device according to claim 1, further comprising a partition disposed between the first display and the second display, the partition being configured to block the left eye of the user from viewing the second display and to block the right eye of the user from viewing the first display.

4. The vision training device according to claim 1, wherein the first display is distinct from the second display.

5. The vision training device according to claim 1, wherein the controller is configured to
control at least one of the first display and the second display to move at least one of the left eye image and the right eye image such that a distance between the left eye image and the right eye image is reduced, and
receive a focus consistency confirmation signal indicating that the image focuses coincide with each other in terms of fusion.

6. The vision training device according to claim 1, wherein
a single display unit includes the first display and the second display, and
the vision training device further comprises a separation filter configured to provide the left eye image and the right eye image to the left eye and the right eye, respectively.

7. The vision training device according to claim 6, wherein the separation filter includes at least one of a color filter and a polarizer.

8. The vision training device according to claim 1, wherein the controller is configured to
set a training range in which fusional vergence training is performed based on the fusional amplitude information of the user, and
control at least one of the first display and the second display to move at least one of the left eye image and the right eye image such that the distance between the left eye image and the right eye image is reduced or increased within the set training range.

9. The vision training device according to claim 8, wherein the controller is configured to set the training range to include the separation distance corresponding to the fusional amplitude information.

10. A vision training method, comprising:
- displaying, on a first display, a left eye image corresponding to a left eye of a user;
- displaying, on a second display, a right eye image corresponding to a right eye of the user;
- controlling at least one of the first display and the second display to move at least one of the left eye image and the right eye image such that image focuses of the left and right eye images coincide with each other in terms of fusion;
- controlling at least one of the first display and the second display to move at least one of the left eye image and the right eye image such that a distance between the left eye image and the right eye image is increased;
- receiving a separation confirmation signal indicating that the image focuses do not coincide with each other in terms of fusion; and
- storing, as fusional amplitude information, information indicating a separation distance between the left eye image and the right eye image when the separation confirmation signal is received.

11. The vision training method according to claim 10, wherein a display unit includes the first display and the second display.

12. The vision training method according to claim 10, wherein a partition is disposed between the first display and the second display, the partition being configured to block the left eye of the user from viewing the second display and to block the right eye of the user from viewing the first display.

13. The vision training method according to claim 10, wherein the first display is distinct from the second display.

14. The vision training method according to claim 10, further comprising:
- controlling at least one of the first display and the second display to move at least one of the left eye image and the right eye image such that the distance between the left eye image and the right eye image is reduced; and
- receiving a focus consistency confirmation signal indicating that the image focuses coincide with each other in terms of fusion.

15. The vision training method according to claim 10, wherein
- a single display unit includes the first display and the second display, and
- a separation filter provides the left eye image and the right eye image to the left eye and the right eye, respectively.

16. The vision training method according to claim 15, wherein the separation filter includes at least one of a color filter and a polarizer.

17. The vision training method according to claim 10, further comprising:
- setting a training range in which fusional vergence training is performed based on the fusional amplitude information of the user; and
- controlling at least one of the first display and the second display to move at least one of the left eye image and the right eye image such that a distance between the left eye image and the right eye image is reduced or increased within the set training range.

18. The vision training method according to claim 17, wherein the setting the training range includes setting the training range to include the separation distance corresponding to the fusional amplitude information.

* * * * *